United States Patent [19]
Lee et al.

[11] Patent Number: 5,545,399
[45] Date of Patent: Aug. 13, 1996

[54] COSMETIC COMPOSITION

[75] Inventors: Caroline M. Lee, Surrey; Martin R. Green, Cambridge, both of Great Britain; Giuseppe Prota, Naples, Italy

[73] Assignee: Chesebrough-Pond's USA Co., Greenwich, Conn.

[21] Appl. No.: 327,727

[22] Filed: Oct. 24, 1994

[30] Foreign Application Priority Data

Oct. 26, 1993 [GB] United Kingdom ............... 9322007

[51] Int. Cl.⁶ .................. A61K 7/42; A61K 31/21; A61K 31/12; A61K 31/075
[52] U.S. Cl. .................. 424/59; 514/529; 514/549; 514/552; 514/679; 514/685; 514/721; 514/734; 560/220; 560/259; 568/325; 568/331; 568/638; 568/660; 568/729
[58] Field of Search ............ 424/59; 514/529, 514/549, 552, 679, 685, 721, 734; 560/220, 259; 568/325, 331, 638, 660, 729

[56] References Cited

FOREIGN PATENT DOCUMENTS

| 0565785 | 10/1993 | European Pat. Off. ........... 424/59 |
| WO94/09756 | 5/1994 | WIPO ........................... 424/59 |

OTHER PUBLICATIONS

International Search Report in International Patent Application GB 94/02335.
Derwent Abstract of JP 5213729.
Kotyk, A. et al., "Inhibition of Phloretin and Phlorizin Derivatives of Sugar Transport in Different Cells", *Biochenische Zeitschrift.*, vol. 342, No. 2, (1965), pp. 129–138.
Abstract of JP1242540, Patent Abstracts of Japan, vol. 13, No. 579.
Abstract of JP4235112, Patent Abstracts of Japan, vol. 16, No. 584.
Chemical Abstract 110:209807.

*Primary Examiner*—Shelley A. Dodson
*Attorney, Agent, or Firm*—Rimma Mitelman

[57] ABSTRACT

A composition for topical application to the skin in order to promote the repair of photo-damaged or aged skin and/or to reduce or prevent damaging effects of ultra-violet light on skin and/or to lighten the skin comprising a hydrocalchone of general structure:

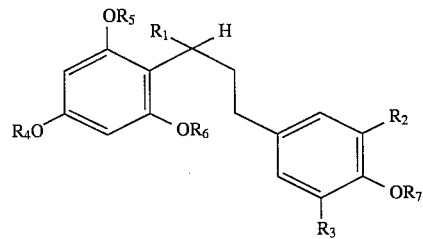

wherein $R_1$, $R_2$ and $R_3$, which may be the same or different, represent H, —OH, —OR or —COR (where R is a $C_{1-20}$ alkyl group);

$R_4$, $R_5$, $R_6$ and $R_7$, which may be the same or different, represent H or —COR (where R is as herein before defined).

Optional additional ingredients include sunscreens and other skin lightening skin lightening agents, particularly retinol or derivatives thereof.

7 Claims, No Drawings

COSMETIC COMPOSITION

The present invention relates to compositions for topical application to human skin and their cosmetic use. In particular, the invention relates to compositions of use in promoting the repair of photo-damaged skin and/or to reduce or prevent the damaging effects of ultra-violet light on skin and/or to lighten the skin. Compositions according to the invention are also of use in the treatment of aged skin.

Problems of hyperpigmentation of skin occur in many situations, including unwelcome general darkening of the skin due to exposure to ultra-violet (UV) light, to genetic makeup, to hyperpigmentation associated with wounds, to age including the appearance of so called 'age spots' and to other factors. There is clearly a need for a safe and effective technique to reduce the degree of pigmentation of the skin in such cases.

Existing methods for reducing skin pigmentation generally involve either killing or damaging the cells which produce the pigment (the melanocytes) for example with hydroquinone or by inhibiting the enzyme, tyrosinase, which catalyses a key step in pigment synthesis for example with kojic acid, ascorbic acid, azelaic acid or catechol and derivatives.

JP 04/235112 (TAC Gijutsu Kagaku Kenkyusho) discloses a tyrosinase inhibitor comprising an active compound of the general formula

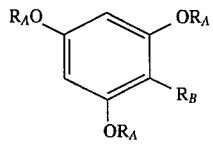

wherein each of $R_A$ is hydrogen or a glucose residue and $R_B$ is hydrogen or the group

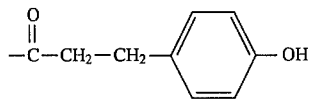

with the proviso that at least one of the $R_A$ groups is hydrogen, however all of the $R_A$ and $R_B$ groups may not be hydrogen.

It is stated that this tyrosinase inhibitor is useful as skin whitening agent for cosmetics and also an agent for preventing darkening of foods.

We have now discovered that specified hydrochalcone structures, in particular dihydrophloretins are capable of suppressing melanin formation in vitro in cultured melanoma cells by a mechanism which involves competitive inhibition of the enzyme tyrosinase. They also have the capacity to act as an antioxidant, so reducing the damaging effects from UV radiation.

Accordingly the invention provides a composition suitable for the topical application to mammalian skin comprising a hydrocalchone of formula (I)

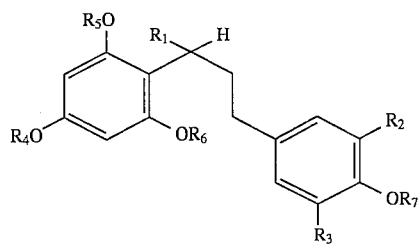

wherein
$R_1$, $R_2$ and $R_3$, which may be the same or different, represent H, —OH, —OR or —COR (where R is a $C_{1-20}$ alkyl group);
$R_4$, $R_5$, $R_6$ and $R_7$, which may be the same or different, represent H or —COR (where R is a $C_{1-20}$ alkyl group).

As used herein, a $C_{1-20}$ alkyl group may be straight or branched chain and is conveniently $C_{1-6}$, preferably $C_{1-4}$ alkyl for example methyl. An alkoxy group is conveniently methoxy or ethoxy. A carboxyalkyl group is conveniently acetoxy.

A preferred class of compounds of formula (I) for use according to the invention has the formula (Ia)

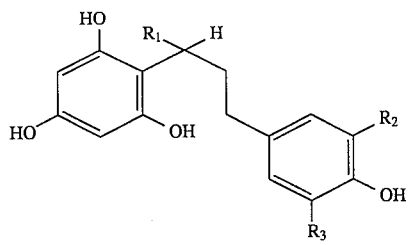

wherein $R_1$, $R_2$ and $R_3$ are as defined herein for formula (I).

In a further preferred class of compounds of formula (I), $R_1$ represents H or —OH.
$R_2$ and $R_3$ preferably represent H.
$R_4$, $R_5$, $R_6$ and $R_7$ preferably represent H.
Preferred hydrochalcones for use according to the invention include: α-deoxyphloretin ($R_1$–$R_7$=H).
A particularly preferred hydrochalcone is dihydrophloretin of formula (II).

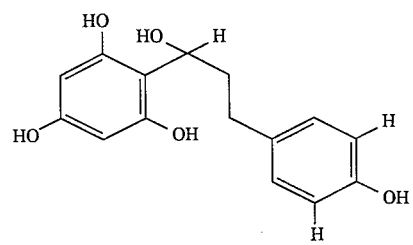

It will be appreciated that compositions according to the present invention may suitably comprise two or more hydrochalcones of formula (I).

Conveniently the amount of hydrochalcone present in the composition according to the invention is from 0.001 to 20%, preferably from 0.01 to 5%, even more preferably from 0.1 to 2% by weight of the composition.

Compounds of formula (I) are either known compounds or may conveniently be prepared from known compounds by methods conventional in the art.

Dihydrophloretin may conveniently be prepared from phloretin (available from Sigma) using one of the following routes:

(a) Phloretin (25 mg) is dissolved in the minimum amount of methanol, diluted with water (3 ml) and treated with a slight excess of $NaBH_4$. After 5 minutes the solution is carefully acidified, with ethyl acetate. The Organic phase is dried over $Na_2SO_4$ and evaporated to dryness to give 17 mg of dihydrophloretin as white powder, homogeneous on TLC analysis (silica gel, $CHCl_3$/MeOH/$H_2O$ 70:28:2).

(b) A solution of phloretin (1 g) in 80% ethanol (20 ml) containing 50 mg of 5% palladium on carbon is stirred under a hydrogen atmosphere. After 6 hrs the mixture is filtered, and the filtrate is concentrated under vacuo to give dihydrophloretin in about 90% yield.

Preferably compositions according to the invention additionally comprise a cosmetically acceptable vehicle to act as a diluent, dispersant or carrier for other materials present in the composition, so as to facilitate their distribution when the composition is applied to the skin.

Vehicles other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmirate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants, such as air, propane, butane, isobutane, dimethyl ether, carbon dioxide, nitrous oxide;

Solvents, such as ethyl alcohol, isopropanol, acetone, ethylene glycol monoethyl ether, diethylene glycol monobutyl ether, diethylene glycol monoethyl ether;

Powders, such as chalk, talc, fuller's earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the emulsion.

The composition of the invention optionally can comprise an organic sunscreen further to enhance the benefit of the composition in providing protection from the harmful effects of excessive exposure to sunlight.

Examples of suitable organic sunscreens, when required, include those set out in Table 1 below, and mixtures thereof.

TABLE 1

| CTFA Name | Trade Name | Supplier |
| --- | --- | --- |
| Benzophenone-3 | UVINUL M-40 | BASF Chemical Co |
| Benzophenone-4 | UVINUL MS-40 | BASF Chemical Co |
| Benzophenone-8 | SPECTRA-SORB UV-24 | American Cyanamide |
| DEA Methoxy-cinnamate | BERNEL HYDRO | Bernal Chemical |

TABLE 1-continued

| CTFA Name | Trade Name | Supplier |
| --- | --- | --- |
| Ethyl dihydroxy-propyl-PABA | AMERSCREEN P | Amerchol Corp |
| Glyceryl PABA | NIPA GMPA | Nipa Labs |
| Homosalate | KEMESTER HMS | Hunko Chemical |
| Methyl anthranilate | SUNAROME UVA | Felton Worldwide |
| Octocrylene | UVINUL N-539 | BASF Chemical Co |
| Octyl dimethyl PABA | AMERSCOL | Amerchol Corp |
| Octyl methoxy-cinnamate | PARSOL MCX | Bernel Chemical |
| Octyl salicylate | SUNAROME WMO | Felton Worldwide |
| PABA | PABA | National Starch |
| 2-Phenyl-benzimidazole--5-sulphonic acid | EUSOLEX 232 | EM Industries |
| TEA salicylate | SUNAROME W | Felton Worldwide |
| 3-(4-methylbenzy-lidene)-camphor | EUSOLEX 6300 | Em Industries |
| Benzophenone-1 | UVINUL 400 | BASF Chemical Co |
| Benzophenone-2 | UVINUL D-50 | BASF Chemical Co |
| Benzophenone-6 | UVINUL D-49 | BASF Chemical Co |
| Benzophenone-12 | UVINUL 408 | BASF Chemical Co |
| 4-Isopropyl dibenzoyl methane | EUSOLEX 8020 | EM Industries |
| Butyl methoxy di-benzoyl methane | PARSOL 1789 | Givaudan Corp |
| Etocrylene | UVINUL N-35 | BASF Chemical Co |

The composition of the invention can accordingly comprise from 0.1 to 10%, preferably from 1 to 5% by weight of an organic sunscreen material.

The composition according to the invention optionally can also comprise as a sunscreen ultrafine titanium dioxide in either of two forms, namely water-dispersible titanium dioxide and oil-dispersible titanium dioxide.

Water-dispersible titanium dioxide is ultrafine titanium dioxide, the particles of which are uncoated or which are coated with a material to impart a hydrophilic surface property to the particles. Examples of such materials include aluminium oxide and aluminium silicate.

Oil-dispersible titanium dioxide is ultrafine titanium dioxide, the particles of which exhibit a hydrophobic surface property, and which, for this purpose, can be coated with metal soaps such as aluminium stearate, aluminium laurate or zinc stearate, or with organosilicone compounds.

By "ultrafine titanium dioxide" is meant particles of titanium dioxide having an average particle size of less than 100 nm, preferably from 10 to 40 nm and most preferably from 15 to 25 nm.

By topical application to the skin of a mixture of both water-dispersible ultrafine titanium dioxide and oil-dispersible ultrafine titanium dioxide, synergically enhanced protection of the skin against the harmful effects of both UV-A and UV-B rays is achievable.

It is believed that this unexpected benefit is due to the deposition of each type of titanium dioxide on different regions of the skin surface, water-dispersible titanium dioxide being preferentially retained by hydrophilic regions of the skin's surface, while oil-dispersible titanium dioxide is retained preferentially by hydrophobic regions of the skin's surface. The combined overall effect is that more efficient physical coverage of the skin's surface is attainable and this can be demonstrated by measurement of the Sun Protection Factor (SPF).

In order to achieve the enhanced, synergistic benefit, as herein described, the weight ratio of water-dispersible titanium dioxide to oil-dispersible titanium dioxide should be from 1:4 to 4:1, preferably from 1:2 to 2:1 and ideally about equal weight proportions.

The total amount of titanium dioxide that can optionally can be incorporated in the composition according to the invention is from 1 to 25%, preferably from 2 to 10% and ideally from 3 to 7% by weight of the composition.

The compositions of the invention optionally can comprise an inorganic sunscreen in addition to ultrafine titanium dioxide as herein defined.

Examples of other inorganic sunscreens include:
zinc oxide, having an average particle size of from 1 to 300 nm,
iron oxide, having an average particle size of from 1 to 300 nm,
silica, such as fumed silica, having an average particle size of from 1 to 100 nm.

It should be noted that silica, when used as an ingredient in the emulsion according to the invention can provide protection from infra-red radiation.

Compositions according to the invention may also optionally comprise other skin whitening agents.

Examples of skin-lightening agents include:
L-ascorbic acid, and derivatives thereof
Kojic acid, and derivatives thereof
Hydroquinone and derivatives thereof
Extract of placenta
Arbutin
dioic acids, especially $C_{6-22}$ dioic acids
α hydroxy acids, such as lactic, malic, tartaric, hydroxycaprylic, citric acids
phloretin
phloridzin
liquorice extract
cysteaminylphenol and derivatives thereof
Niacin
Niacinamide, and
Compounds having the structure (III)

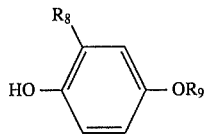

where $R_8$ represents H, or an ether group represented by $OR_{10}$, $R_9$ and $R_{10}$ are the same or different and each represents a group chosen from branched or unbranched alkyl or alkenyl groups having up to 20 carbon atoms.

In a preferred aspect, the composition according to the invention may additionally comprise retinol or a derivative thereof having the structure (IV)

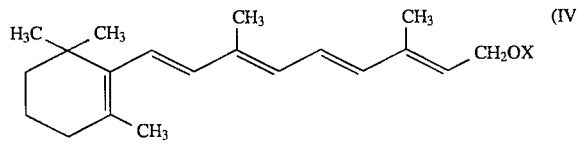

where X represents H or —$COR_{11}$ where $R_{11}$ represents a group chosen from branched or unbranched, alkyl or alkenyl groups having up to 20 carbon atoms.

In addition to retinol itself, examples of derivatives of retinol include:
Retinyl acetate
Retinyl butyrate
Retinyl propionate
Retinyl octanoate
Retinyl laurate
Retinyl palmitate
Retinyl oleate
Retinyl linoleate The amount of retinol, or a derivative thereof, present in the composition according to the invention is from 0,001 to 10% and preferably 0,005 to 1% by weight of the composition, most preferably 0.01 to 0.5% by weight of the composition.

Preferably the composition comprises retinol, most preferable the composition comprises the trans-isomer of retinol.

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lipophilic balance (HLB) of the emulsifier employed.

The composition according to the invention can optionally comprise one or more oils or other materials having the properties of an oil.

Examples of suitable oils include mineral oil and vegetable oils, and oil materials, such as those already proposed herein as emollients. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

The composition according to the invention can also optionally comprise one or more emulsifiers the choice of which will normally determine whether a water-in-oil or and oil-in-water emulsion is formed.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 2 in which the chemical name of the emulsifiers is given together with an example of a trade name as commercially available, and the average HLB value.

TABLE 2

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Polyoxyethylene (2) stearyl ether | Brij 72 | 4.9 |
| Polyoxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan | Tween 61 | 9.6 |

TABLE 2-continued

| Chemical Name of Emulsifier | Trade Name | HLB Value |
|---|---|---|
| monostearate | | |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene (8) monostearate | Myrj 45 | 11.1 |
| PEG 400 monooleate | Emerest 2646 | 11.7 |
| PEG 400 monostearate | Tegester PEG 400 | 11.9 |
| Polyoxyethylene 10 monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |
| Polyoxyethylene (9.3) octyl phenol | Triton X-100 | 13.0 |
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene 20 sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention.

It is to be understood that two or more emulsifiers can be employed if desired.

The amount of emulsifier or mixtures thereof, that optionally can be incorporated in the composition of the invention is from 1 to 50%, preferably from 2 to 20% and most preferably from 2 to 10% by weight of the composition.

The composition of the invention can also comprise water, usually up to 80%, preferably from 5 to 80% by volume.

Emulsifiers or surfactants in the form of silicone polymers may be incorporated into compositions of the invention in place of or in addition to the optional emulsifier(s) already mentioned.

Suitable silicone surfactants are high molecular weight polymers, particularly of dimethyl polysiloxane with polyoxyethylene and/or polyoxypropylene side chains having a molecular weight of from 10,000 to 50,000.

The dimethyl polysiloxane polymer is conveniently provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane.

Examples of the volatile siloxanes in which the polysiloxane polymer can be dispersed include polydimethyl siloxane (pentamer and/or hexamer).

A particularly preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be up to 25%, preferably from 0.5 to 15% by weight of the emulsion.

Examples of conventional adjuncts which can optionally be employed include preservatives, such as para-hydroxy benzoate esters; antioxidants, such butylated hydroxytoluene; humectants, such as glycerol, sorbitol, 2-pyrrolidone-5-carboxylic acid, dibutylphthalate, gelatin, polyethylene glycol, such as PEG 200–600; buffers, such as lactic acid together with a base such as triethanolamine or sodium hydroxide; waxes, such as beeswax, ozokerite wax, paraffin wax; plant extracts, such as aloe vera, cornflower, witch hazel, elderflower, cucumber; thickeners; activity enhancers; colourants; and perfumes. Cosmetic adjuncts can form the balance of the composition.

The composition according to the invention is intended primarily as a skin-care product for topical application to human skin to repair photo-damaged skin and to prevent photo-damage to skin due to exposure to sunlight. In particular, the composition can be used to reduce skin blotchiness and mottling due to hyperpigmentation, to improve skin texture with reductions in fine wrinkling and otherwise to improve skin colour. In general, the composition, when topically applied to skin, is useful in the prevention and or treatment of actinic damage to all skin cells.

Accordingly, the invention provides the cosmetic use of a composition comprising a hydrochalcone having the general structure (I) as hereinbefore defined.

In an alternative aspect the invention provides the use of a composition comprising a hydrochalcone of formula (I) in the manufacture of a medicament for treating skin.

The invention further provides a method of treating skin comprising topically administering thereto a composition comprising a hydrocalchone having the general structure (I).

The compositions according to the invention may be formulated in conventional manner using one or more cosmetically and/or pharmaceutically acceptable carriers or excipients.

EXAMPLES

Test method—In vitro melanocyte cell culture

Pigment producing cells derived from a mammalian melanoma are grown in culture by standard methods. Preferred cell lines are B16 or S-91 cells, but other lines or primary mouse or human melanocytes can be used.

Melanoma cells are grown in cell culture medium such as RPMI 1640 (GIBCO) supplemented with fetal calf serum and glutamine to approximately ⅓ confluence. The active is dissolved in culture medium, the pH adjusted as required and sterile filtered. The solution is then added to the cells.

The cells are cultured for a further period of 4 days and the amount of melanin produced assayed by measuring the absorbance at 540 nm of the melanin released into the medium.

Cell viability in the presence of the inhibitor is tested using neutral red (3-amino-7-dimethylamino-2-methyl phenazine hydrochloride) a water soluble vital dye which passes through the intact plasma membrane and becomes concentrated in lysosomes of viable cells. For any culture, the amount of dye taken up is proportional to the number of viable cells and agents that damage cell and lysosomal membranes inhibit dye incorporation.

The cells are incubated in 50 μg/ml neutral red solution for 3 hours at 37° C. in 5% $CO_2$ in air. The solution is aspirated, the cells washed once in saline and to them added a solvent (50% $H_2O$, 49% ethanol, 1% acetic acid) to solubilise the dye. The amount of neutral red dye is quantified by measuring absorbance at 540 nm.

Results

The above procedure was used to assess the ability of compositions of (a) dihydrophloretin alone and (b) dihydrophloretin plus retinol to reduce the amount of melanin produced. No adverse effects are seen on cell viability at any level of dihydrophloretin or retinol tested, indicating that pigment inhibition is due to specific inhibition of melanogenisis and not cell toxicity.

The results for melanin production were calculated as percentages of control which contained medium alone. Results are given in Tables 3 to 5. There was no effect on viability at the concentrations of actives reported.

TABLE 3

| Dihydrophloretin (mM) | % of control melanin production |
|---|---|
| 0 | 100 |
| 0.01 | 100 |
| 0.03 | 99.8 |
| 0.3 | 57 |

TABLE 4

| Trans Retinol | Dihydrophloretin (mM) | | | | |
|---|---|---|---|---|---|
| (μm) | 0 | 0.1 | 0.17 | 0.23 | 0.3 |
| 0 | 100 | 98.1 | 109.0 | 109.3 | 108.7 |
| 2.0 | 120.9 | 120.2 | 111.0 | 110.0 | 104.0 |
| 6.7 | 92.9 | 82.1* | 76.0* | 60.9* | 34.0* |

*Percentage is significantly less (P<0.05) than Control.

TABLE 5

| RETINOL | | DIHYDROPHLORETIN (mM) | | | | |
|---|---|---|---|---|---|---|
| (μM) | | 0.0 | 0.1 | 0.17 | 0.23 | 0.3 |
| 0 | % pigmentation | 100 | 99 | 104 | 104 | 94 |
|  | % viability | 100 | 100 | 100 | 100 | 100 |
|  | n | 4 | 3 | 3 | 3 | 4 |
| 2.0 | % pigmentation | 120 | 120 | 111 | 110 | 104 |
|  | % viability | 100 | 100 | 100 | 100 | 100 |
|  | n | 1 | 1 | 1 | 1 | 1 |
| 6.7 | % pigmentation | 97 | 86 | 73 | 55 | 34 |
|  | % viability | 100 | 100 | 100 | 100 | 100 |

TABLE 5-continued

| RETINOL | DIHYDROPHLORETIN (mM) | | | | |
|---|---|---|---|---|---|
| (μM) | 0.0 | 0.1 | 0.17 | 0.23 | 0.3 |
| n | 2 | 2 | 2 | 2 | 1 |

EXAMPLE 1

This example illustrates a lotion according to the invention.

| Ingredient | % w/w |
|---|---|
| dihydrophloretin | 2.0 |
| silicone surfactant | 10 |
| volatile siloxane | 14 |
| mineral oil | 1.5 |
| titanium dioxide (water-dispersible) | 2.5 |
| titanium dioxide (oil-dispersible) | 2.5 |
| 2-hydroxyoctanoic acid | 1 |
| 2-hydroxypropanoic acid | 5 |
| butylene glycol | 10 |
| sodium chloride | 2 |
| 1-proline | 0.1 |
| neutralising agent | qs |
| preservative | qs |
| perfume | qs |
| water | qs |

EXAMPLE 2

This example illustrates a fluid cream according to the invention.

| Ingredient | % w/w |
|---|---|
| retinyl acetate | 0.3 |
| dihydrophloretin | 1.0 |
| volatile siloxane (DC 345) | 8.2 |
| silicone surfactant (DC 3225C) | 12 |
| petroleum jelly | 0.5 |
| mineral oil | 1.5 |
| Parsol MCX (octyl methoxycinnamate) | 3 |
| titanium dioxide (oil-dispersible) | 2 |
| titanium dioxide (water-dispersible) | 2 |
| sodium chloride | 2 |
| butylene glycol | 10 |
| 1-proline | 0.1 |
| 2-hydroxyoctanoic acid | 1 |
| 2-hydroxypropanoic acid | 5 |
| neutralising agent | qs |
| preservative | qs |
| perfume | qs |
| water | qs |

EXAMPLE 3

This example illustrates a cream according to the invention.

| Ingredient | % w/w |
|---|---|
| retinyl palmitate | 1 |
| α-deoxyphloretin | 0.1 |
| volatile siloxane (DC 345 Fluid) | 8.2 |
| silicone surfactant (DC 3225C) | 12 |
| mineral oil | 1.5 |
| petroleum jelly | 0.5 |
| Parsol MCX (octyl methoxycinnamate) | 1.5 |

| Ingredient | % w/w |
| --- | --- |
| titanium dioxide (oil-dispersible) | 1.0 |
| titanium dioxide (water-dispersible) | 1 |
| 2-hydroxyoctanoic acid | 1 |
| 2-hydroxypropanoic acid | 5 |
| sodium chloride | 2 |
| butylene glycol | 10 |
| 1-proline | 0.1 |
| neutralising agent (aqueous phase to 4.5) | qs |
| preservative | qs |
| perfume | qs |
| water | to 100 |

In the same manner, a cream containing 0.1% w/w retinol in place of the retinyl palmirate and 0.1% w/w dihydrophloretin in place of α-deoxyphloretin may be prepared.

EXAMPLE 4

This example illustrates a lotion according to the invention.

| Ingredient | % w/w |
| --- | --- |
| dihydrophloretin | 1.0 |
| silicone surfactant (DC 3225C) | 10 |
| volatile siloxane (DC 345) | 14 |
| mineral oil | 1.5 |
| Parsol MCX | 3 |
| titanium dioxide (oil-dispersible) | 2 |
| titanium dioxide (water-dispersible) | 2 |
| butylene glycol | 10 |
| sodium chloride | 2 |
| 1-proline | 0.1 |
| 2-hydroxyoctanoic acid | 1 |
| 2-hydroxypropanoic acid | 5 |
| neutralising agent | qs |
| perfume | qs |
| preservative | qs |
| water | qs |

EXAMPLE 5

This example also illustrates a sunscreen cream in accordance with the invention.

| Ingredients | % w/w |
| --- | --- |
| retinyl acetate | 0.2 |
| retinyl laurate | 0.2 |
| dihydrophloretin | 0.5 |
| cetyl dimethicone copolyol | |
| cetyl dimethicone | |
| polyglyceryl-3-oleate | * 5 |
| hexyl laurate | |
| isopropyl myristate | 13.5 |
| beeswax | 3 |
| silicone fluid 200 | 5 |
| preservatives | 0.5 |
| titanium dioxide (water-dispersible) | 2.5 |

| Ingredients | % w/w |
| --- | --- |
| titanium dioxide (oil-dispersible) | 2.5 |
| water | to 100 |

*available is ABIL W508 ex Goldschmidt

We claim:

1. A composition for topical application to human skin comprising (i) from 0.001 to 20% of a hydrochalcone of formula (Ia):

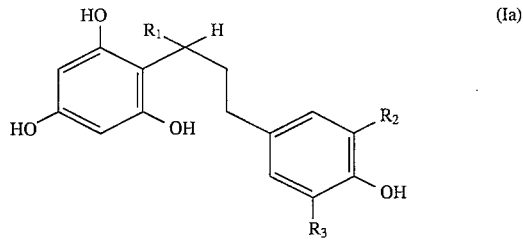

wherein $R_1$, $R_2$ and $R_3$, which may be the same or different, represent H, OH, —OR or —COR; where R is a $C_{1-20}$ alkyl group;

(ii) from 0.001% to 10% of retinol or a derivative thereof having the structure (IV):

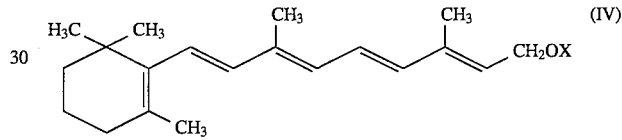

wherein X represents H or $COR_{11}$, $R_{11}$ represents a branched or unbranched, alkyl or alkenyl group having up to 20 carbon atoms; and (iii) a cosmetically acceptable vehicle in an amount of from 10 to 99.999%.

2. A composition according to claim 1 wherein $R_2$ and $R_3$ in formula (Ia) represent H and $R_1$ represents H or —OH.

3. A composition according to claim 1 wherein the hydrochalcone of formula (Ia) is dihydrophloretin.

4. A composition according to claim 1 wherein the hydrocalchone is present in an amount of from 0.1 to 2% by weight of the composition.

5. A composition according to claim 1 comprising trans-retinol.

6. A method for repairing photo-damaged or aged skin and preventing damage to skin due to exposure to ultra-violet light comprising topically applying an effective amount of the composition of claim 1 to the skin.

7. A method for whitening skin pigmentation comprising topically applying an effective amount of the composition of claim 1 to the skin.

* * * * *